(12) United States Patent
Tompkins (10) Patent No.: US 9,161,848 B2
(45) Date of Patent: Oct. 20, 2015

(54) SYSTEMS AND METHODS FOR PROSTHETIC SUSPENSION SYSTEM

(71) Applicant: Michael E. Tompkins, Austin, TX (US)

(72) Inventor: Michael E. Tompkins, Austin, TX (US)

(73) Assignee: Hanger, Inc., Austin, TX (US)

( * ) Notice: Subject to any disclaimer, the term of this patent is extended or adjusted under 35 U.S.C. 154(b) by 0 days.

(21) Appl. No.: 13/754,553

(22) Filed: Jan. 30, 2013

(65) Prior Publication Data

US 2014/0039643 A1    Feb. 6, 2014

Related U.S. Application Data (60) Provisional application No. 61/593,225, filed on Jan. 31, 2012.

(51) Int. Cl.
| | | |
|---|---|---|
| *A61F 2/80* | (2006.01) | |
| *A61F 2/74* | (2006.01) | |
| *A61F 2/50* | (2006.01) | |
| *A61F 2/78* | (2006.01) |

(52) U.S. Cl.
CPC ............ *A61F 2/80* (2013.01); *A61F 2/7812* (2013.01); *A61F 2002/5083* (2013.01); *A61F 2002/742* (2013.01); *A61F 2002/7818* (2013.01); *A61F 2002/805* (2013.01)

(58) Field of Classification Search
CPC ................. A61F 2002/802; A61F 2002/805; A61F 2002/807
See application file for complete search history.

(56) References Cited

U.S. PATENT DOCUMENTS

| | | | |
|---|---|---|---|
| 2,897,512 A * | 8/1959 | Sackett | ............................ 623/39 |
| 5,258,037 A | 11/1993 | Caspers | |
| 5,376,132 A | 12/1994 | Caspers | |
| 5,534,034 A | 7/1996 | Caspers | |
| 5,549,709 A | 8/1996 | Caspers | |
| 5,571,208 A | 11/1996 | Caspers | |
| 5,685,479 A | 11/1997 | Weber-Caspers | |
| 5,735,906 A | 4/1998 | Caspers | |
| 5,904,722 A | 5/1999 | Caspers | |
| 6,287,345 B1 * | 9/2001 | Slemker et al. | ................. 623/34 |
| 6,508,842 B1 | 1/2003 | Caspers | |
| 6,554,868 B1 | 4/2003 | Caspers | |
| 6,645,253 B2 | 11/2003 | Caspers | |
| 6,726,726 B2 | 4/2004 | Caspers | |
| 6,761,742 B2 | 7/2004 | Caspers | |
| 6,926,742 B2 | 8/2005 | Caspers et al. | |
| 6,960,546 B2 | 11/2005 | Caspers et al. | |
| 6,974,484 B2 | 12/2005 | Caspers | |
| 7,150,762 B2 | 12/2006 | Caspers | |

(Continued)

FOREIGN PATENT DOCUMENTS

| | | | | |
|---|---|---|---|---|
| DE | 100 26 399 A1 * | 12/2001 | ................ A61F 2/60 |
| GB | 2 069 847 A * | 9/1981 | ...................... 623/34 |

(Continued)

*Primary Examiner* — David H Willse
(74) *Attorney, Agent, or Firm* — Foley & Lardner LLP (57) ABSTRACT

A prosthetic device includes an inner socket assembly including an upper interface member having a generally cylindrical outer periphery, the outer periphery defining a diameter and a length, the diameter being substantially greater than the length, and an outer socket assembly including a lower interface member having a recess correspondingly-shaped to the outer periphery of the upper interface member. At least a portion of the upper interface member is received within the recess of the lower interface member to secure the inner socket assembly to the outer socket assembly.

18 Claims, 5 Drawing Sheets

(56) References Cited

U.S. PATENT DOCUMENTS

| | | |
|---|---|---|
| 7,922,775 B2 | 4/2011 | Caspers |
| 8,114,167 B2 | 2/2012 | Caspers |
| 2007/0021841 A1* | 1/2007 | Al-Temen et al. ............... 623/25 |
| 2007/0168045 A1* | 7/2007 | Slemker et al. ................ 623/34 |
| 2008/0243266 A1* | 10/2008 | Haynes et al. .................. 623/34 |

FOREIGN PATENT DOCUMENTS

| | | | | |
|---|---|---|---|---|
| GB | 2 228 201 A | * | 8/1990 | ................ A61F 2/60 |
| SU | 1598999 A1 | * | 10/1990 | ................ A61F 2/00 |

* cited by examiner

SYSTEMS AND METHODS FOR PROSTHETIC SUSPENSION SYSTEM

CROSS-REFERENCE TO RELATED PATENT APPLICATIONS

This application claims the benefit of U.S. Provisional Application No. 61/593,225, filed Jan. 31, 2012, which is incorporated by reference herein in its entirety.

BACKGROUND

The present disclosure relates generally to the field of prosthetic devices, and more specifically, to a suspension system usable with prosthetic devices such as lower limb prosthetics.

There are many challenges associated with providing an effective means of supporting, for example, a lower residual portion of a leg, within a prosthetic device. As such, various embodiments disclosed herein related to improved systems and methods of prosthetic device suspension systems.

SUMMARY

One embodiment relates to a prosthetic device comprising an inner socket assembly comprising an upper interface having a generally cylindrical outer periphery, the outer periphery having a diameter substantially greater than a length; an outer socket assembly comprising a lower interface having a recess correspondingly-shaped to the outer periphery of the upper interface; wherein at least a portion of the upper interface is received within the recess of the lower interface to secure the inner socket assembly to the outer socket assembly.

Another embodiment relates to a prosthetic device, comprising an inner socket assembly having a lower portion defining a disc-shaped adapter; an outer socket assembly comprising a receptacle configured to releasably engage the inner socket assembly; wherein the interface of the disc-shaped adapter and the receptacle acts to secure the inner socket assembly to the outer socket assembly.

Another embodiment relates to a prosthetic device, comprising an inner socket assembly configured to receive a portion of a residual limb of a user; an outer socket assembly configured to receive at least a portion of the inner socket assembly; and an interface mechanism configured to releasably secure the inner socket assembly to the outer socket assembly during use of the prosthetic device by a user, the interface mechanism comprising a generally cylindrical member provided on one of the inner socket assembly and the outer socket assembly; and a receptacle provided on the other of the inner socket assembly and the outer socket assembly and having a recess configured to releasably secure the outer socket assembly to the inner socket assembly in a non-rotational manner.

BRIEF DESCRIPTION

The present disclosure will become more fully understood from the following detailed description, taken in conjunction with the accompanying drawings, wherein like reference numerals refer to like elements.

DETAILED DESCRIPTION OF EXEMPLARY EMBODIMENTS

Referring generally to the FIGURES, various embodiments of prosthetic devices are shown according to exemplary embodiments. Though various embodiments herein are described in the context of an artificial leg, it is contemplated that the present disclosure is equally applicable to other contexts in which a device is connected to a user's body. For example, the device could be an artificial arm, an orthotic component, or another prosthetic/orthotic product that uses similar methods to connect to a user. The connection method need not be a fully encompassing socket like a prosthesis. Further, a vacuum could assist a connection device or may be used as a stabilizer in connection with various connection methods.

A conventional lower leg prosthetic device may include an inner liner, or inner socket, that receives a residual limb and is coupled to a more rigid outer frame, or outer socket. To couple the inner liner to the frame, relatively long, narrow pins may be used in conjunction with a locking mechanism such as a ratchet, clutch, or strangulation mechanism. However, these types of pin connection mechanisms often have drawbacks, such as vertical movement of the pin, wobbling of the pin, wear of the locking mechanism, or improper operation of the pin/locking mechanism due to infiltration of dirt, debris, etc.

Furthermore, relatively long, narrow pins may have a small point of contact between the inner liner and the frame, which may result in additional problems related to the mechanical suspension of the inner socket within the frame, including movement (e.g., wobbling, etc.) between the inner socket and the frame, undesirable transfer of pressure to the distal end of the residual limb (e.g., due to vertical movement of the pin during the heel strike motion, resulting in "tightening" of pin connection), and/or undesirable "pistoning" from slack in the pin locking mechanism permitting vertical movement between inner liner and rigid frame. Pistoning may in turn lead to "milking" of the residual limb (e.g., the repetitive application and release of downward forces and/or pressures on the residual limb). Furthermore, during the "swing phase" of a patient's gate, most or all of the pressure relating to retaining the prosthesis on the residual limb may be concentrated on the pin.

Various embodiments disclosed herein may address one or more of these concerns by providing improved systems and methods of suspension for prosthetic devices. Some embodiments may be usable in a "retrofit" application to modify existing pin locking mechanism arrangements. Other embodiments may be usable in new devices to provide an improved suspension system for patients.

Figure 1:
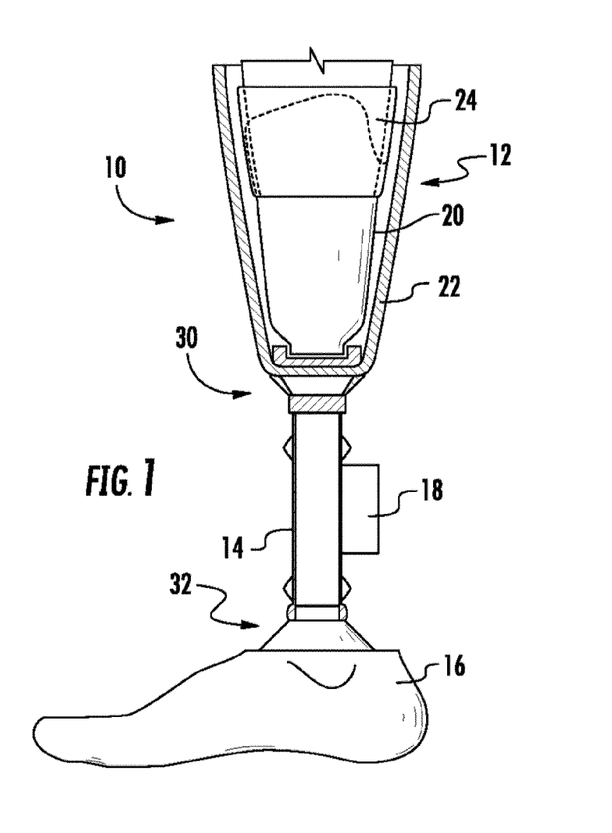
FIG. 1 is a side view of a prosthetic device secured to a residual limb according to an exemplary embodiment.
Figure 2:
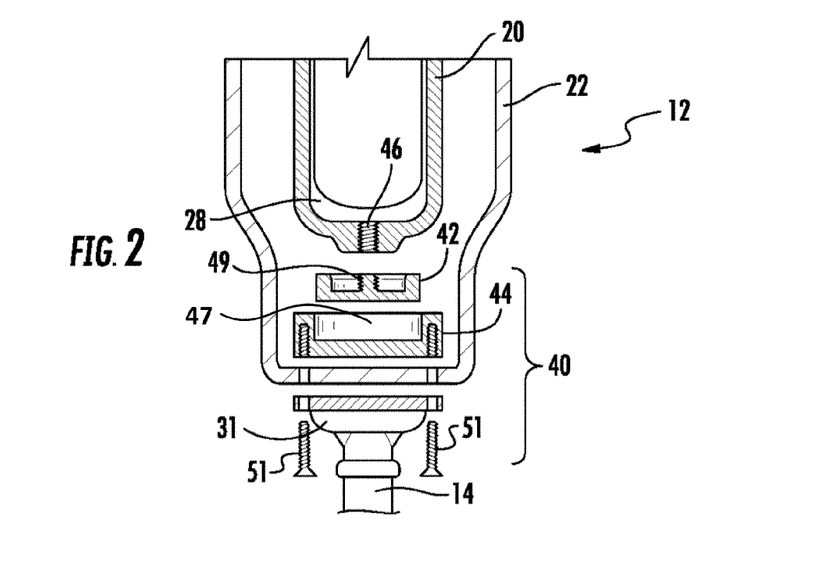
FIG. 2 is an exploded view of a portion of a prosthetic device according to an exemplary embodiment.

Referring now to FIGS. 1-2, a prosthetic device 10 is shown according to an exemplary embodiment. Device 10 includes a socket assembly 12, a pylon 14, an artificial foot 16, and a control system 18. Device 10 is intended to restore functionality to patients having lost limbs such as legs, arms, and the like. Generally, socket assembly 12 receives a portion of a residual limb of a user. Pylon 14 is a mechanical structure that provides a mechanical support and interface between socket assembly 12 and artificial foot 16. Artificial foot 16 may be designed to replicate a real foot (or, similarly, a hand, etc., depending on the particular application). As described in greater detail below, control system 18 controls an amount of vacuum applied to the socket assembly 12, where the vacuum provides a negative pressure to maintain the residual limb securely in place within the socket assembly. Based on various factors, control system 18 may vary the vacuum applied to socket assembly 12 to optimize the performance of device 10 for users.

Referring further to FIGS. 1-2, according to one embodiment, a residual limb of a user is received within an inner liner or socket 20 (e.g., a flexible or semi-rigid liner or socket). Inner liner 20 may be configured to fit around the residual limb and into an outer socket or frame 22 (e.g., a rigid frame or socket, etc.). In some embodiments, inner liner 20 may be formed of a gel or silicone material, while other materials may be used according to various other alternative embodiments. The particular size and/or shape of inner liner 20 may vary depending on the user and the particular device 10 being utilized. According to one embodiment, inner liner 20 is sized to avoid discomfort to the user and/or improper fit of device 10.

According to an exemplary embodiment, frame 22 may be provided with a size and shape customized to a particular user such that a substantial portion of a residual limb may be received within the interior of frame 22. An additional liner may be applied to the residual limb prior to insertion into inner liner 20. As shown in FIG. 2, a cavity 28 may remain after insertion of the residual limb into inner liner 20 and prior to application of a vacuum to socket assembly 12. A desired vacuum may be applied to cavity 28 to provide a proper fit between the residual limb and inner liner.

According to an exemplary embodiment, a sealing sleeve 24 (see FIG. 1) may be configured to form an airtight seal between the residual limb and inner liner 20. For example, sealing sleeve 24 may in some embodiments be a non-foamed, nonporous polyurethane suspension sleeve that rolls over and covers a portion of inner liner 20 and a portion of the residual limb. The inner surface of sealing sleeve 24 may provide a seal against the skin on the user's thigh and the outer surface of inner liner 20 to provide an airtight seal for the vacuum. Sealing sleeve 24 may be applied over the outer surface of inner liner 20 and rolled up onto the thigh portion of the residual limb to provide a vacuum seal and enable device 10 to achieve appropriate vacuum (measured in, e.g., inches of mercury) and prosthetic suspension.

According to an exemplary embodiment, pylon 14 is attached to socket assembly 12 at an upper portion 30 of pylon 14. Lower portion 32 of pylon 14 may be coupled to and/or form a part of artificial foot 16. Any suitable coupling means may be used to couple pylon 14 to artificial foot 16. According to an exemplary embodiment, artificial foot 16 is configured to substantially replicate an actual human foot in shape, size, and/or range of motion. As indicated above, while the embodiments disclosed herein generally refer to a lower limb prosthetic device used in connection with an artificial foot, the teachings herein extend to other applications, including upper limb prosthetics and other devices that would benefit from the features disclosed herein. Artificial foot 16 may be made any suitable material, and the shape, size, and other characteristics of artificial foot 16 may be varied from those described herein to suit a particular user and/or application.

According to an exemplary embodiment, pylon 14 is fixedly secured to frame 22, e.g., via a pyramid/pylon adapter 31. Inner liner 20 may be coupled to frame 22 via an interface or coupling mechanism 40. According to various exemplary embodiments, coupling mechanism 40 provides a mechanical coupling or suspension system between liner 20 and frame 22/pylon 14. As discussed in greater detail herein, mechanism 40 may provide various benefits relative to more traditional coupling systems having relatively long, narrow pin locking mechanisms.

Figure 8:
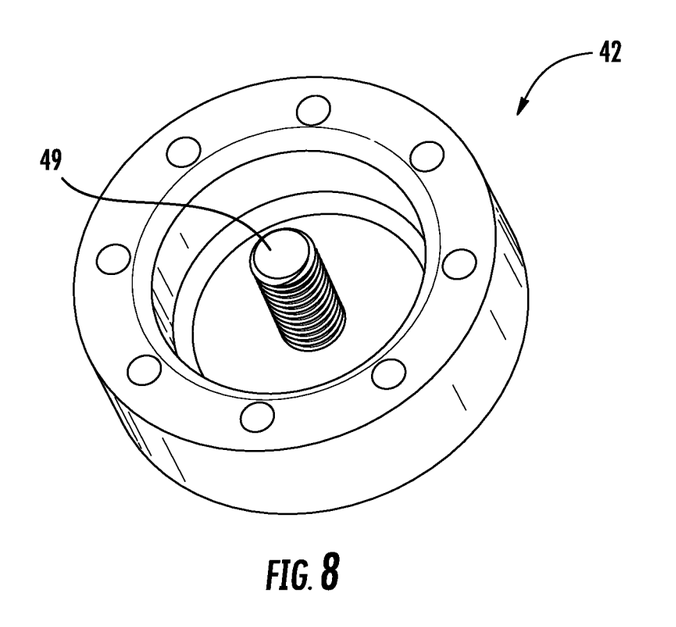
FIG. 8 is a perspective view of an adapter usable with a prosthetic device according to an exemplary embodiment.

Referring to FIG. 2, a portion of a prosthetic device such as device 10 is shown according to an exemplary embodiment and includes coupling mechanism 40. As shown in FIG. 2, mechanism 40 includes an adapter 42 (e.g., a generally cylindrical member, a disc-shaped member, etc.) and a receptacle 44 (e.g., a member having a generally cylindrical recess, etc.), and acts to couple inner liner 20 to frame 22 via adapter 42 and receptacle 44. For example, in one embodiment, inner liner 20 may include a threaded insert 46. Threaded insert 46 may be usable to receive a threaded pin to couple inner liner 20 to frame 22 in a conventional manner. Adapter 42 may have a central threaded portion 49 (see FIG. 8) that may be threadingly received by threaded insert 46 to form an upper interface or coupling portion of coupling mechanism 40. Adapter 42 and/or receptacle 44 may be made of any suitable metal, plastic, or composite material.

Receptacle 44 may be secured to frame 22 and pylon 14 using, for example, one or more fasteners 51. As shown in FIG. 2, one or more fasteners may extend upward through pylon 31 and frame 22 and into receptacle 44. Receptacle 44 may extend upward from the inner bottom of frame 22 and be configured to engage adapter 42. For example, as shown in FIG. 2, receptacle 44 may have a generally cylindrical outer periphery and a recess 47 formed therein (e.g., by a generally circular sidewall). In one embodiment, recess 47 is correspondingly shaped to adapter 42 such that at least a portion of adapter 42 is configured to be releasably received by recess 47. For example, a user may insert a portion of a residual limb inside of inner liner 20, with adapter 42 attached to a bottom portion thereof. In order to secure inner liner 20 to frame 22 having receptacle 44 attached thereto, the user may insert the liner/adapter into the interior of the frame until adapter 42 engages receptacle 44 to securely fasten inner liner 20 to frame 22.

Adapter 42 may be releasably coupled to receptacle 44 using a variety of suitable methods. For example, in some embodiments, the geometry of adapter 42 and receptacle 44 may be such that a "snap-fit" engagement (e.g., by way of indents/detents, interfering structural portions, etc.) between the outer periphery (or portions thereof) of adapter 42 and recess 47. In other embodiments, a variety of latches, spring-loaded retention members, and other securement devices may be utilized. For example, one or both of adapter 42 and/or receptacle 44 may include a spring-loaded or biased projection intended to engage a corresponding surface or recess upon mating of the adapter and receptacle.

According to an exemplary embodiment, adapter 42 comprises a generally cylindrical outer surface, at least a portion of which is received by recess 47. For example, adapter 42 may have a diameter that is substantially greater than its length (e.g., measured along a longitudinal axis of the prosthetic device). For example, the diameter of adapter 42 (e.g. the engagement portion of adapter 42 that interferes with receptacle 44) may be approximately 2, 3, or 4 times its length. According to other embodiments, the diameter of adapter 42 may be larger or smaller relative to the length of adapter 42. Providing an adapter 42 having an increased diameter, and therefore a relatively large bottom surface area, acts to increase the surface area over which forces may be transmitted between frame 22 and inner liner 20 (and potentially, the residual limb of a user). Furthermore, an increase in the surface area of the interface between frame 22 and inner liner 20 may provide a more stable connection and avoid undesirable movement between frame 22 and inner liner 20 during use of prosthetic device 10 by a user.

Figure 3:
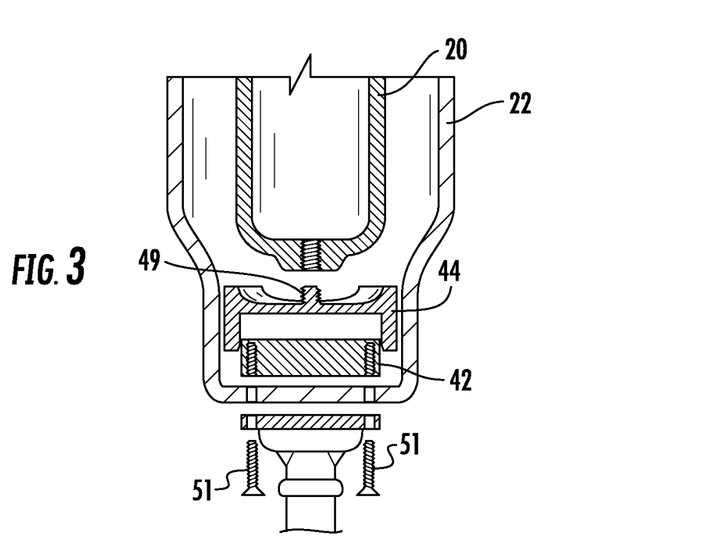
FIG. 3 is an exploded view of a portion of a prosthetic device according to another exemplary embodiment.

As shown in FIG. 2, coupling mechanism 40 may be usable to retrofit more traditional pin locking mechanisms that utilize a threaded insert in inner liner 20. Furthermore, as shown in FIG. 3, the relative positions of adapter 42 and receptacle 44 may be reversed, such that receptacle 44 may be attached to inner liner 20 and adapter 42 may be attached to frame 22. Further yet, rather than accommodating liners and frames originally intended to be used with a pin locking mechanism in a retrofit application, coupling mechanism 40 may be integrated into inner liner 20 and/or frame 22, as discussed in greater detail with response to FIGS. 4-5.

Figure 4:
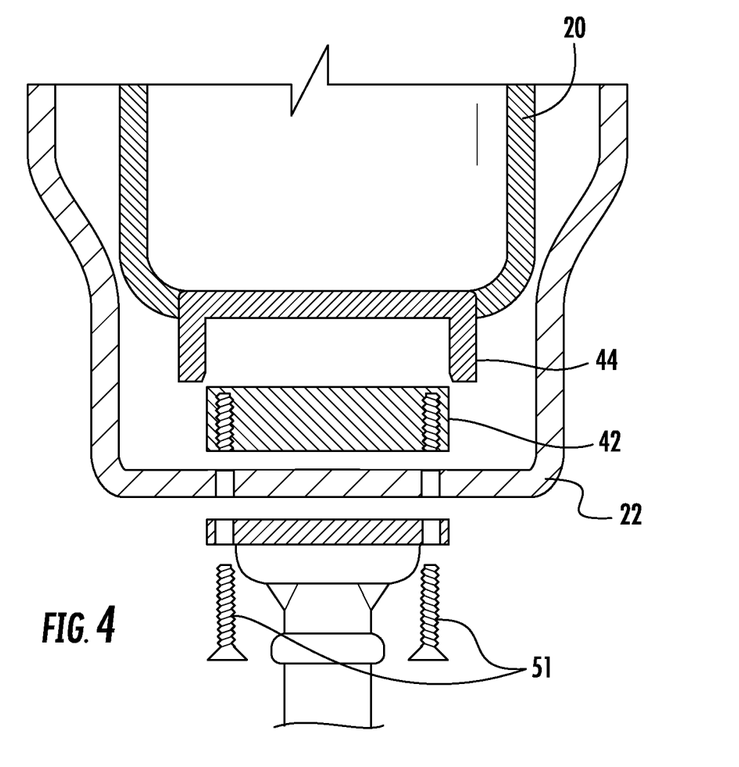
FIG. 4 is an exploded view of a portion of a prosthetic device according to another exemplary embodiment.
Figure 5:
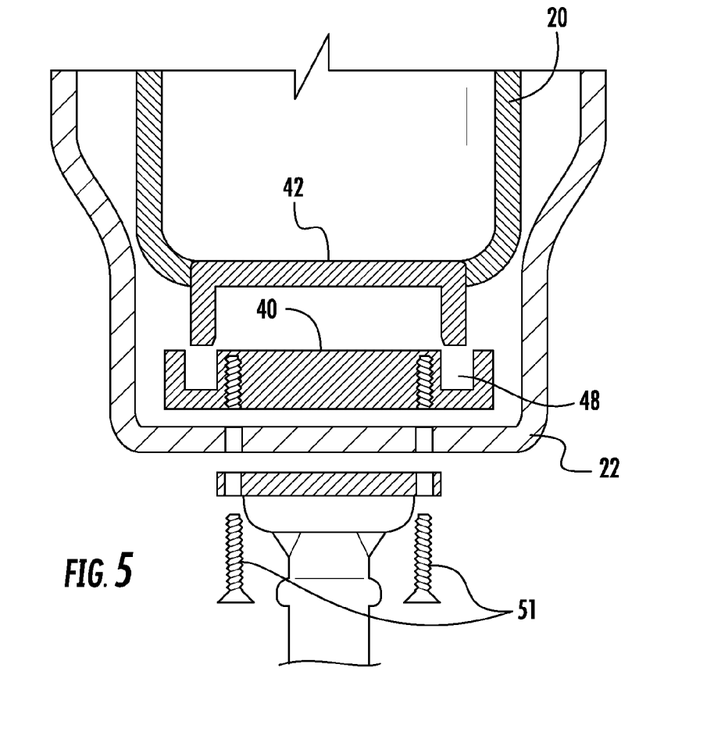
FIG. 5 is an exploded view of a portion of a prosthetic device according to another exemplary embodiment.

Referring now to FIG. 4, inner liner 20 is shown to have receptacle 44 integrated therewith. In one embodiment, receptacle 44 may be molded or cast with the bottom portion of inner liner 20, such that threaded insert 46 (see, e.g., FIG. 2) is not required. As with the embodiments of FIGS. 2-3, the relative positions of adapter 42 and receptacle 44 may be reversed, such that adapter 42 may in some embodiments be integrated with inner liner 20. Similarly, adapter 42 or receptacle 44 may be integrated into frame 22 in yet further embodiments.

According to some embodiments, receptacle 44 substantially surrounds at least a portion of the peripheral sidewalls (e.g., cylindrical sidewalls) of adapter 22. In other embodiments, as shown for example in FIG. 5, adapter 42 may include an annular slot, or recess 48, such that the outer walls of receptacle 44 that form recess 47 are received within slots 48, thus forming interlocking walls/recesses between adapter 42 and receptacle 44. The configuration of FIG. 5 may provide added stability for users by providing another means for preventing relative motion between inner liner 20 and frame 22.

In some embodiments, coupling mechanism 40 includes structural features (e.g., a keyed portion, non-circular geometries, indents/detents, etc.) intended to prevent relative rotational motion between adapter 42 and receptacle 44, and in turn, inner liner 20 and frame 22. Any suitable anti-rotational structural features may be used according to various alternative embodiments.

Figure 7:
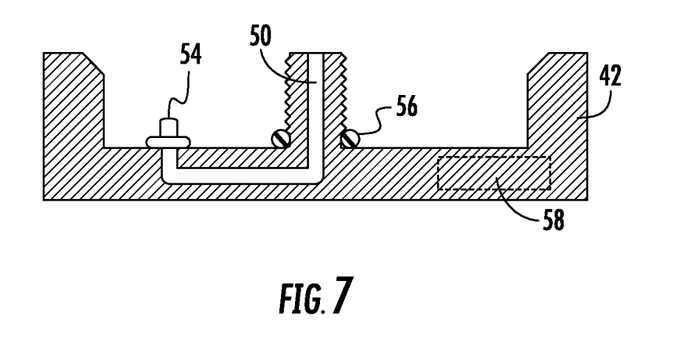
FIG. 7 is a cross-sectional view of an adapter usable with a prosthetic device according to an exemplary embodiment.

According to any of the embodiments discussed herein, a vacuum may be provided to secure the residual limb within inner liner 20. A vacuum pump 58 (see FIG. 7) may be connected to socket assembly 12 via a fluid connection that provides fluid communication between the pump and cavity 28 of socket assembly 12. Any suitable pump may be utilized (e.g., a diaphragm pump driven by a DC motor, etc.). Operation of pump 58 creates a partial vacuum in cavity 28 that in turn secures the residual limb to socket assembly 12. Vacuum pump 58 may be coupled to pylon 14, or located at other locations on device 10. For example, according to one embodiment, pump 58 may be provided within or adjacent either adapter 42 and/or receptacle 44.

Figure 6:
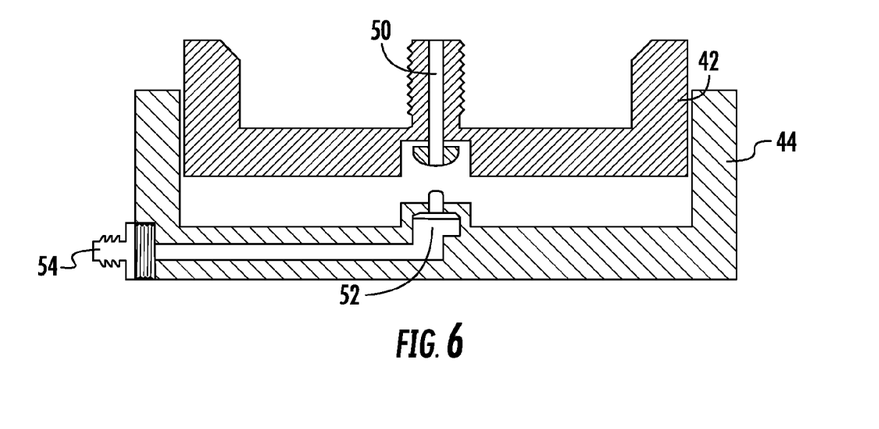
FIG. 6 is an exploded view of a portion of a prosthetic device according to another exemplary embodiment.

Referring to FIG. 6, receptacle 44 is shown to include an upstanding valve 52 configured to provide fluid communication with cavity 28 via a passageway 50. Receptacle 44 may further provide a fluid communication between valve 52 and a port 54 (e.g., a barbed port, etc.) which communicates with a vacuum source (e.g., a vacuum pump coupled to or integrated into device 10). Alternatively, referring to FIG. 7, a vacuum pump and/or associated controlling electronics (e.g., an electronic controller to control operation of the vacuum pump) may be disposed within or at least partially within adapter 42 (or similarly, receptacle 44). An o-ring 56 may be provided to ensure an air-tight seal between adapter 42 and surrounding components (e.g., inner liner 22, etc.) and a vacuum port may connect a pump 58 with, for example, cavity 28, by way of passageway 50. Other configurations of vacuum pumps, ports, and associated passageways may be used according to various alternative embodiments.

Figure 9:
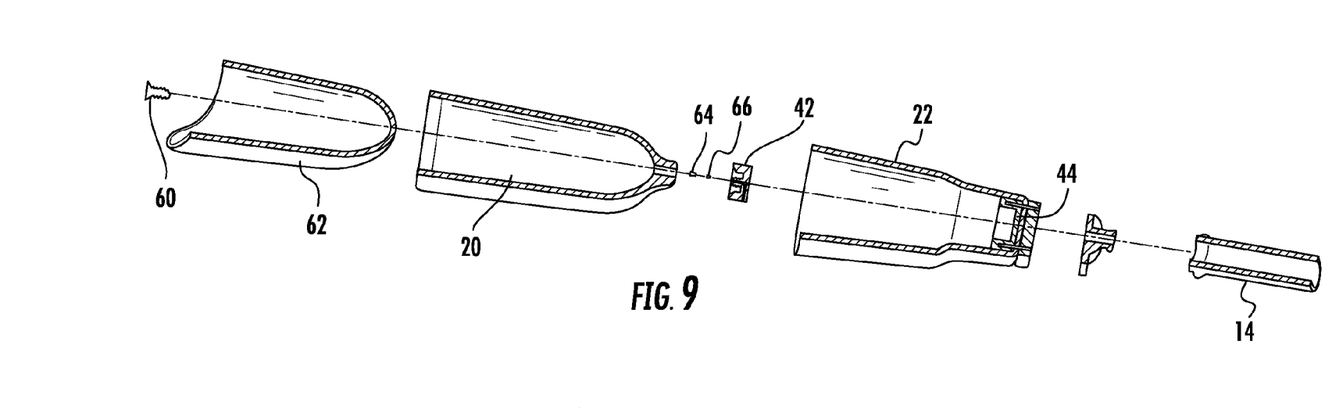
FIG. 9 is an exploded view of a prosthetic device according to another exemplary embodiment.
Figure 10:
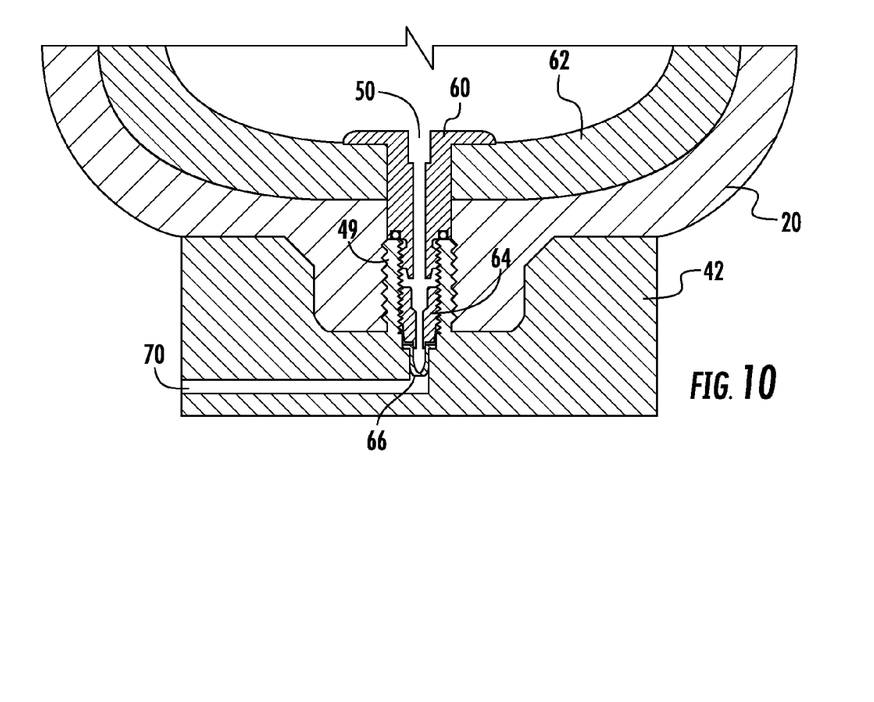
FIG. 10 is a cross-section view of a portion of the prosthetic device of FIG. 9 according to an exemplary embodiment.

Referring to FIGS. 9-10, in some embodiments a check valve may be used to control the pressure within the inner sleeve. For example, a valve assembly may be integrated into adapter 42 as shown in FIG. 9. According to one embodiment, the valve assembly is a check valve assembly and includes a liner lock 60, a sealing member such as an o-ring, a check valve retainer 64, and a check valve 66. Liner lock 60 extends through an additional liner 62 (e.g., a polyethylene liner) and inner liner 20 and threadingly engages adapter 42. Check valve 66 is configured to permit air to flow out of, but not into, the prosthetic device, and to permit exhausted air to exit via a channel and port 70. As a user inserts inner liner 20 into frame 22 (not shown in FIG. 10), air may be exhausted through the valve assembly and out from adapter 20, generating a partial vacuum within the socket assembly. This configuration may generate vacuum during initial insertion of inner liner 20 into frame 22, and during use of the prosthetic device (e.g., during walking), to take advantage of a user's weight in generating vacuum within the prosthetic device. In some embodiments, the valve assembly may be used in conjunction with a separate vacuum system to provide additional vacuum to the prosthetic device.

It is important to note that the construction and arrangement of the elements of the prosthetic device as shown in the exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the embodiments. For example, for purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to mechanical, fluid, or electrical relationship between the two components. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. A prosthetic device comprising:
an inner socket assembly comprising:
an inner liner configured to fit around a residual limb of a person and into an outer socket, and
an upper interface member having a generally cylindrical outer periphery, the outer periphery defining a diameter and a length, the diameter being substantially greater than the length, the upper interface member removably coupled to the inner liner via a threaded connection;
an outer socket assembly comprising:
the outer socket, and
a lower interface member having a recess correspondingly-shaped to the outer periphery of the upper interface member; and
a pylon;
wherein the lower interface member is secured to the pylon by a fastener that extends upward through the pylon, through the outer socket, and into the lower interface member;
wherein at least a portion of the upper interface member is received within the recess of the lower interface member to secure the inner socket assembly to the outer socket assembly, wherein the inner socket assembly is secured to the outer socket assembly via a snap-fit connection between the outer periphery of the upper interface member and the recess of the lower interface member.

2. The device of claim 1, wherein the inner liner includes a first threaded portion, wherein the upper interface member includes a second threaded portion, wherein the first threaded portion and the second threaded portion form the threaded connection.

3. The device of claim 1, further comprising a vacuum pump configured to generate a vacuum within the inner socket assembly, wherein the vacuum pump is in fluid communication with an interior of the inner socket assembly via at least one of the upper interface member and the lower interface member.

4. The device of claim 3, wherein the vacuum pump is provided at least partially within at least one of the upper interface member and the lower interface member.

5. The device of claim 4, wherein the upper interface member is rotationally fixed relative to the lower interface member.

6. The device of claim 3, wherein the lower interface member includes an upstanding valve in fluid communication with the vacuum pump such that when the inner socket assembly is secured to the outer socket assembly, the vacuum pump is in fluid communication with the interior of the inner socket assembly via the upstanding valve and a passageway through the upper interface member.

7. A prosthetic device, comprising:
an inner socket assembly having an inner liner configured to fit around a residual limb of a person and configured to fit into an outer socket, and a lower portion defining a disc-shaped adapter, wherein the lower portion is removably coupled to the inner liner via a threaded connection;
an outer socket assembly comprising the outer socket, and a receptacle configured to releasably engage the lower portion of the inner socket assembly; and
a pylon;
wherein the receptacle is secured to the pylon by a fastener that extends upward through the pylon, through the outer socket, and into the lower interface member;
wherein an interface between the disc-shaped adapter and the receptacle acts to secure the inner socket assembly to the outer socket assembly, wherein the inner socket assembly is secured to the outer socket assembly via a snap-fit connection formed between the disc-shaped adapter and the receptacle.

8. The device of claim 7, wherein the disc-shaped adapter comprises a diameter substantially greater than its length.

9. The device of claim 7, wherein the disc-shaped adapter comprises a circular recess configured to receive a circular sidewall of the receptacle.

10. The device of claim 7, wherein the disc-shaped adapter is configured to provide fluid communication between a vacuum pump and an interior of the inner socket assembly.

11. The device of claim 7, further comprising a vacuum pump at least partially disposed within at least one of the disc-shaped adapter and the receptacle.

12. A prosthetic device, comprising:
an inner socket assembly configured to receive a portion of a residual limb of a user, the socket assembly including an inner liner configured to fit around the residual limb of the user and a first connecting component, the first connecting component coupled to the inner liner via a threaded connection;
an outer socket assembly configured to receive at least a portion of the inner socket assembly;
a pylon; and
an interface mechanism configured to releasably secure the inner socket assembly to the outer socket assembly during use of the prosthetic device by a user, the interface mechanism comprising:
the first connecting component; and
a second connecting component provided on the outer socket assembly, the second connecting component interfacing with the first connecting component to releasably secure the outer socket assembly to the inner socket assembly in a non-rotational manner;
wherein the second connecting component is secured to the pylon by a fastener that extends upward through the pylon, through the outer socket assembly, and into the second connecting component;
wherein the inner socket assembly is releasably secured to the outer socket assembly via a snap-fit connection formed between the first connecting component and the second connecting component.

13. The device of claim 12, wherein the interface mechanism prevents relative rotational movement of the inner socket assembly and the outer socket assembly.

14. The device of claim 12, wherein the first connecting component includes a cylindrical member that has a width substantially greater than its length.

15. The device of claim 12, further comprising a valve assembly disposed within the interface mechanism.

16. The device of claim 15, wherein the valve assembly comprises a check valve configured to permit air to exhaust from a cavity defined between the residual limb and the inner liner.

17. The device of claim 12, further comprising a vacuum pump configured to generate a vacuum between the inner liner and the residual limb.

18. The device of claim 17, wherein the vacuum pump is coupled to the interface mechanism.

* * * * *